United States Patent [19]

Sington

[11] 4,238,158

[45] Dec. 9, 1980

[54] VISUAL INVESTIGATION METHOD

[76] Inventor: Edward P. C. Sington, New Amberden Hall, Deben Green, Saffron Walden, Essex, England

[21] Appl. No.: 18,615

[22] Filed: Mar. 8, 1979

[30] Foreign Application Priority Data

Mar. 15, 1978 [GB] United Kingdom ............... 10289/78

[51] Int. Cl.³ ............................................. G01N 21/01
[52] U.S. Cl. ..................... 356/241; 73/151; 250/256
[58] Field of Search ................ 356/237, 239, 241, 36, 356/256, 51; 350/179, 319, 321; 250/301, 256; 73/151, 155; 354/63

[56] References Cited

U.S. PATENT DOCUMENTS

| 2,677,996 | 5/1954 | Laval, Jr. ............................. 354/63 |
| 2,953,979 | 9/1960 | Rosene et al. ......................... 354/63 |
| 2,982,191 | 5/1961 | Laval, Jr. ........................... 354/129 X |
| 3,113,455 | 10/1963 | Sloan et al. ............................ 73/155 |
| 3,596,582 | 8/1971 | Sayer ................................. 73/151 X |

*Primary Examiner*—John K. Corbin
*Assistant Examiner*—Bruce Y. Arnold
*Attorney, Agent, or Firm*—Lyon & Lyon

[57] ABSTRACT

The in situ visual inspection of down-hole equipment in drilling and exploration wells is effected by forming an optically clear region at the desired level and by using suitable video apparatus within the region so formed. This is achieved by introducing an optically clear liquid which is substantially immiscible with, and which has a density similar to that of the opaque liquid such as mud or crude oil which is present in the well. The density of the optically clear liquid can be controlled by blending two or more compatible components, e.g. as a liquid mixture or as a solution of a solid in a liquid.

10 Claims, No Drawings

VISUAL INVESTIGATION METHOD

This invention relates to methods for the visual location and inspection of objects obscured by opaque liquids. In particular, the invention is designed to facilitate the inspection of objects and materials used in the construction of production and exploration wells, especially oil wells.

Despite the many advanced techniques employed in the recovery of oil from subterranean formations there remain various basic problems for which no facile solution has yet been found. For example corrosion and wear of the tubing used in production wells and the casing used in exploration wells is an ever-present problem and it is frequently necessary to shut down the wells and remove whole sections of tubing or casing for inspection. Similar considerations apply to the need for regular inspection of other down-hole equipment, such as pressure control valves. Further problems arise when a drill bit becomes stuck or breaks during drilling, a complex "fishing" operation being needed to locate and repair or retrieve the stuck or broken part. The problems involved in carrying out such operations in oil or thick mud at depths of 10,000 feet or more will be obvious.

OBJECTS OF THE INVENTION

It is an object of the invention to provide a relatively facile method for the in situ visual inspection of down-hole equipment in production and exploration wells used in the recovery of oil and other valuable materials from the earth.

It is a further object of the invention to provide a method for producing a region of relative optical clarity at a desired level in an opaque liquid which comprises introducing at said level an optically clear liquid which is substantially immiscible with and which has a density similar to that of said opaque liquid.

The process of the present invention is especially applicable to solving the problems discussed above in connection with the exploration for oil and, for convenience, the invention will now be described in more detail mainly with reference to such applications. However, it will be appreciated that the invention may equally well be applied to other fields of geological exploration, to mining, to certain industrial processes in which opaque liquids are present, and to various other fields of art.

By means of the present invention it is possible to provide a stable region of optical clarity at any desired depth in the opaque liquid thereby permitting the use of suitable video devices which, in the case of a drilling hole, can relay a picture to the surface, thus providing an easy and definitive method of inspection as well as a means of monitoring any necessary operation at the critical position.

The essence of the present invention lies in selecting an optically clear liquid which is immiscible with the opaque liquid, i.e. in most cases immiscible with water, and introducing it at a desired location in the opaque liquid so as to produce an optically clear region. In order to maintain the stability of the clear region it is desirable to introduce a sufficient quantity of clear liquid to produce a "fluid lock", i.e. a sufficient quantity of clear liquid to separate the opaque liquid above and below the clear liquid into discrete regions. Under these conditions, it can be shown that the net upthrust or downthrust on the clear liquid is reduced or eliminated, even when there is a difference in density between the clear liquid and the opaque liquid; thus a stable region is produced.

The clear liquid should be sufficiently immiscible with the opaque liquid that it is able to form a discrete phase.

If the difference in density between the clear liquid and the opaque liquid is too great, it will not be possible to establish a satisfactory fluid lock, since the clear liquid on being introduced into the opaque fluid will be subject to strong positive or negative (upward or downward) Archimidean forces. These will tend to break up the clear liquid into globules, which will then float or sink away from the region. In most cases this means that the density of the clear liquid must lie within ±10%, preferably ±5%, more especially ±2% of that of the opaque liquid. However, when the viscosity or yield point of the opaque liquid is sufficiently high, it may be possible to employ clear liquids with greater density differences than these.

Without wishing to limit the invention by theoretical explanation, it is believed that the maximum radius of a droplet which can be supported in a fluid without sinking is given by $$r = 3Y/(\Delta\sigma)(g) \, y$$

where
r = radius of droplet in cm
Y = yield-point of medium in dynes/cm$^2$
$\Delta\sigma$ = difference in specific gravity between droplet and medium
g = acceleration due to gravity in cm/sec$^2$.

Taking a typical yield-point for the mud of 50 this means that the maximum radius will be about 1.6 cm at a difference in specific gravity between clear liquid and the mud of 0.1. Thus when the clear liquid is injected into the mud a drop will be completely supported by it until it reaches a diameter of 3.2 cm. Thereafter it will tend to sink until a fluid lock is achieved. However, the viscosities at the low rates of shear are very high and the rate of sinking will be correspondingly low. It is thought, therefore, that a maximum difference in specific gravity of about 0.2 will be satisfactory in most cases, but lower maximum values of, for example, 0.1 may be necessary if the diameter of the bore hole is high.

In practice, density matching has to be carried out at the given location. This may be done, for example, by determining the density of a sample of the opaque liquid at that position and then adjusting the density of an optically clear liquid formed from two or more components.

The density of drilling mud usually lies within the range of from 1.1 to 2.0 grams/ml and may be varied during drilling to take account of changing conditions. It will be appreciated therefore that it is not always practicable to inject an unmodified liquid to form the region of optical clarity because of the effect of the Archimidean forces hereinbefore described, unless its density was sufficiently close to the particular mud density in that region at that time.

In some cases the necessary density matching may be effected by dispersing in a clear liquid a particulate solid having substantially the same refractive index as the liquid so that it is, in consequence, invisible when dispersed, although it will be appreciated that, in certain applications, exact optical compatibility will be less important. However, in most cases it will be preferred to obtain the desired density match by the use of two or more compatible optically clear liquids. One especially suitable liquid which may be used as a base for densities within the above range is carbon tetrachloride, which has a density of about 1.6. This may be blended with other optically clear liquids, especially hydrocarbons, to produce densities of desired lower values.

If, for any reason, an initial injection of clear liquid fails to produce a completely clear region, but, instead, produces a region in which residual murkiness is caused by regions of mud adhereing to the sides of, for example, the drill hole or to a lower incompletely formed interface of the clear region, it will sometimes be possible to effect clarity by the introduction of a further clear liquid of a slightly higher density which coalesces with the liquid of the already formed partially clear region and thus produces a region of greater overall specific gravity. This increase in specific gravity may cause the remaining regions of mud to break off from the walls of the bore hole or from the lower interface and float upwardly to the roof of the clear region. The further liquid added may, in some applications, be introduced above the initially formed first clear region in such a manner that it sinks downwardly and gradually coalesces with the initial clear liquid.

Yet another way in which an optically clear liquid of the required density may be produced is by the dissolution of solid compounds, especially metal salts, e.g. those of relatively dense metals with relatively high molecular weight organic acids, in suitable liquid media. For example, lead stearate and barium stearate may be dissolved in carbon tetrachloride to give optically clear liquids of densities greater than 1.6.

It will be understood that this invention is not limited to circumstances in which the opaque liquid is aqueous in nature. For example, in one further important application of the present invention, a visual inspection is carried out in a production oil well. In this case the opaque liquid consists of crude oil and the clear immiscible liquid may be a mixture of water and a lower alcohol such as methanol, or water itself or any other liquid substantially immiscible with the crude oil.

Obviously it will be necessary to introduce the optically clear liquid in a manner which allows a coherent region to be formed. In particular, it will be necessary that the liquid should be introduced through an aperture which has a sufficiently large area that the formation of small encapsulated droplets is avoided. However, suitable means of introduction can readily be determined by routine trial and experiment and the apparatus used will, in any case, vary according to the specific application. The length of time for which the optically clear region need remain clear will, of course, depend on the particular application concerned. If necessary, one or more further portions of optically clear liquid may be introduced into an already-formed region in order to prolong the life thereof. However, one surprising advantage of the present invention is that migration of mud particles in the optically clear region is, in many cases, completely absent. A further surprising feature is that, in some cases, the stability of the locked clear system is so high that it may even be moved up and down within the bore hole by circulating the mud whilst at the same time still avoiding substantial migration of the mud particles into the clear liquid.

It will be appreciated that, in many applications of the present invention, the optically clear region which is created will be relatively inaccessible so that inspection by the naked eye or by other direct visual methods will be impossible. It will, therefore, be necessary in such applications to employ suitable video devices and these will obviously have to be constructed to suit the particular application. For example a video device for use in a bore hole will have to be housed in a material which is capable of withstanding very high hydrostatic pressures and will have to be provided with thermal insulation to protect its electrical and electronic components from the relatively high temperatures liable to be encountered. However, again, the optimum nature and the construction of the video devices can readily be determined in any given situation. In some applications it may be more appropriate to use a video device employing infra-red radiation and it will be appreciated that the terms "visual investigation", "optical clarity", etc. as used in this specification do not limit the invention to applications employing light within the visible range.

EXAMPLES

In all the following Examples the apparatus used consisted of a glass cylinder 12" high and of 1½" diameter and closed at its lower end. A funnel with rubber tubing fitted to its stem and provided with a screw clip to regulate flow was clamped above the tube of the glass cylinder and the tubing extended down into the cylinder so that its lower end was about ⅔rds of the way down. The fluids were dropped by a simple gravity feed mechanism taking care to avoid the production of air bubbles.

EXAMPLE 1

The cylinder was filled with water, a blend of carbon tetrachloride and toluene of specific gravity 1.00±0.01 was prepared and 30 mls of the blend were injected ⅔rds down the cylinder. A stable region was formed when the injection rate was 5 ml/sec.

EXAMPLE 2

Example 1 was repeated but using a 5.5% bentonite dispersion (specific gravity 1.03) in place of the water. This dispersion had an apparent viscosity of 25 cps and a shear strength of about 60 dynes/cm$^2$. In addition, the lower end of the tube was plugged and two staggered slits were cut on opposite sides of the tube in order to produce horizontal injection of the clear fluid. A stable region was formed, but the clear region was not readily visible from the outside of the tube because of the presence of regions of mud adhering to the inside wall of the cylinder.

Without emptying the cylinder an attempt was made to introduce a second clear region above the first using a fluid of much higher density that the bentonite mud in order to ascertain whether the yield-point of the mud was sufficient to prevent sinking of the fluid before a fluid lock could be established. Pure carbon tetrachloride (specific gravity 1.6) was used, but when it was added it sank downwardly into the mud to the first clear region. However, at the same time the films of mud cleared from the walls of the cylinder and the region assumed the form of a well developed band with flat interfaces at the top and bottom.

EXAMPLE 3

Using the procedure of Example 2 a clear fluid of a higher viscosity was injected into the 5.5% bentonite dispersion, the clear fluid being used being a blend of dibutyl phthalate (specific gravity 1.047) and toluene (specific gravity 0.867). Provided that steps were taken to avoid air locks in the tube, a stable clear region was formed.

EXAMPLE 4

Various experiments were conducted using bentonite dispersions of 4.5 and 5.0% using different blends of carbon tetrachloride and kerosene (specific gravity 0.77) as the clear liquid. It was found that for both dispersions it was possible to obtain only a somewhat unstable region when the difference in the specific gravity of the mud and the clear liquid was as high as 0.2 but, provided that the difference was kept to about 0.1, satisfactory results were obtained.

EXAMPLE 5

Using the procedure of Example 2, the cylinder was filled with crude oil (specific gravity 0.94) and 30 ml of a 1:3 blend of methanol and water was injected ⅔ of the way down the cylinder. At an injection rate of 5 ml/sec a clear stable region formed at this level.

From the above examples it will be apparent to those skilled in the art that, the results obtainable will depend somewhat on the nature and physical characteristics of the clear fluid and on the manner of its introduction into the opaque liquid. However, given the basic concept of the present invention, the most appropriate parameters for a given situation can readily be ascertained by routine trial and experiment. They will appreciate, therefore, that the present invention provides greatly improved investigation techniques within optically unclear liquids.

Other modifications and applications falling within the basic concept of the present invention will be apparent to those skilled in the art.

I claim:

1. A method of carrying out a visual inspection at a desired level in an opaque liquid in a bore hole, an exploration well, a production well or the like used in the recovery of oil or other valuable materials from a subterranean formation, said method comprising the steps of
   (a) forming a region of relative optical clarity at said level by introducing an optically clear liquid which is substantially immiscible with, and which has a density similar to, that of the opaque liquid present at said level, and
   (b) introducing suitable visual inspection means into the region of relative optical clarity so produced and effecting an in situ inspection.

2. A method as claimed in claim 1, wherein the density of the optically clear liquid is controlled by blending two or more compatible components.

3. A method as claimed in claim 2, wherein the optically clear liquid is a blend of two or more liquids.

4. A method as claimed in claim 3, wherein the opaque liquid is mud and at least one of said optically clear liquids is selected from carbon tetrachloride, toluene, dibutyl phthalate, dimethyl phthalate and kerosene.

5. A method as claimed in claim 3, wherein the opaque liquid is crude oil and a least one of said optically clear liquids is selected from the group consisting of water and lower alcohols.

6. A method as claimed in claim 5, wherein the optically clear liquid is a blend of water and methanol.

7. A method as claimed in claim 2, wherein the optically clear liquid is a solution of one or more solid compounds in an optically clear liquid.

8. A method as claimed in claim 7, wherein the optically clear liquid is a solution in carbon tetrachloride of a compound selected from the group consisting of lead stearate and barium stearate.

9. A method as claimed in claim 1, wherein the density of an initially formed optically clear region is subsequently adjusted by the addition of a further optically clear liquid.

10. A method as claimed in claim 1, wherein the difference in specific gravity between the clear liquid and the opaque liquid is not greater than 0.2.

* * * * *